(12) United States Patent
Frasch et al.

(10) Patent No.: US 8,003,316 B2
(45) Date of Patent: *Aug. 23, 2011

(54) POLARIZATION-ENHANCED DETECTOR WITH GOLD NANORODS FOR DETECTING NANOSCALE ROTATIONAL MOTION AND METHOD THEREFOR

(75) Inventors: Wayne D. Frasch, Phoenix, AZ (US); Lars Chapsky, Tempe, AZ (US)

(73) Assignee: Arizona Board of Regents, Acting for and on Behalf of Arizona State University, Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/538,534

(22) PCT Filed: Dec. 11, 2003

(86) PCT No.: PCT/US03/39435
§ 371 (c)(1),
(2), (4) Date: Jun. 10, 2005

(87) PCT Pub. No.: WO2004/053501
PCT Pub. Date: Jun. 24, 2004

(65) Prior Publication Data
US 2006/0110738 A1   May 25, 2006

Related U.S. Application Data

(60) Provisional application No. 60/432,589, filed on Dec. 11, 2002.

(51) Int. Cl.
*C12Q 1/68* (2006.01)
*C12M 3/00* (2006.01)
*C07H 21/04* (2006.01)
(52) U.S. Cl. .............. 435/6; 435/287.2; 536/24.3
(58) Field of Classification Search .............. None
See application file for complete search history.

(56) References Cited

U.S. PATENT DOCUMENTS

| | | | | |
|---|---|---|---|---|
| 3,972,619 A | * | 8/1976 | Stevens | 356/369 |
| 5,305,139 A | * | 4/1994 | Greenberg | 359/390 |
| 6,232,066 B1 | * | 5/2001 | Felder et al. | 435/6 |
| 6,449,088 B1 | * | 9/2002 | Pettingell et al. | 359/386 |
| 2002/0160485 A1 | * | 10/2002 | Firman | 435/199 |

OTHER PUBLICATIONS

Yu-Ying Yu et al. Gold Nanorods: Electrochemical Synthesis and Optical Properties. 1997. The Journal of Physical Chemistry B. vol. 101 No. 34 pp. 6661-6664.*
Kudo, Seishi et al. Abrupt changes in flagellar rotation observed by laser dark field microscopy. 1990 Nature. vol. 346. pp. 677-680.*
Sonnichsen, C et al. Drastic Reduction of Plasmon Damping in Gold Nanorods. 2002. Physical Review Letters. vol. 88. No. 7 pp. 1-4.*
Mock, JJ et al. Composite Plasmon Resonant Nanowires. 2002. Nano Letters. vol. 2 No. 5. pp. 465-469.*
Yasuda, Ryohei et al. Resolution of distinct rotational substeps by submillisecond kinetic analysis of F1-ATPase, Apr. 2001, Nature, vol. 410 pp. 898-904.*
Yasuda et al., "Resolution of distinct rotational substeps by submillisecond kinetic analysis of F1-ATPase", Nature, 410:898-904, 2001.
Panne et al., "The McrBC Endonuclease Translocates DNA in a Reaction Dependent on GTP Hydrolysis", J. Mol. Biol., 290:49-60, 1999.

* cited by examiner

*Primary Examiner* — Amanda Shaw
(74) *Attorney, Agent, or Firm* — George A. Leone; Citadel Patent Law

(57) ABSTRACT

A nanoscale motion detector attaches a gold nanorod (30) to the rotating arm (26) of a molecular structure (10) to cause the nanoparticle to rotate. The molecular structure is an F1-ATPase enzyme. The gold nanorod is exposed to a light source. The long axis of the gold nanorod scatters red light when the nanorod is in a first position. The short axis of the gold nanorod scatters green light when the nanorod is in a second position. A polarizing filter filters the red and green light to detect the rotational motion by observing alternating red and green lights. A detection DNA stand (50) is coupled between the gold nanorod and the molecular structure. The detection DNA strand hybridizes with a target DNA strand (58) if the target DNA strand matches the detection DNA strand to form a structural link between the molecular structure and gold nanorod.

6 Claims, 3 Drawing Sheets

US 8,003,316 B2

POLARIZATION-ENHANCED DETECTOR WITH GOLD NANORODS FOR DETECTING NANOSCALE ROTATIONAL MOTION AND METHOD THEREFOR

CLAIM TO DOMESTIC PRIORITY

This application is a U.S. National Stage Application filed under 35 U.S.C. 371 claiming priority from the International Application No. PCT/US2003/039435, filed Dec. 11, 2003, which claims the benefit of U.S. Provisional Patent Application Ser. No. 60/432,589, filed Dec. 11, 2002, and which applications are incorporated herein by reference.

FIELD OF THE INVENTION

The present invention relates in general to motion detectors and, more particularly, to a detector and method of detecting motion on the nanometer scale.

BACKGROUND OF THE INVENTION

When working with man-made materials and naturally occurring substances, engineers and scientists are accustomed to observing and measuring physical characteristics and behavioral phenomena such as size, shape, dimensions, transformation, motion, and other cause and effect relationships on the micrometer (μm) scale. For example, in the electronics and semiconductor industry, the dimensions of devices are measured in terms of microns. In biotechnology applications, most instruments and techniques used to observe physical characteristics and behavioral phenomena, including microscopes, optical imaging, and electron micrographs are also in the micrometer range.

As technology advances, the dimensions of devices, materials, and substances of interest continue to dramatically shrink in size. Significant research and development is underway in what is commonly known as nanotechnology, i.e., devices and materials that exist and operate in the range of 1 to 1000 nanometers (nm). It has been said that the ultimate refinement of realization and sensitivity is a single molecule. With nanotechnology, work is often done at the molecular level. Complex processes can take place in such a small space that the application become very portable. Propagation times and energy consumption are negligible.

Nanotechnology finds applications in characterizing and monitoring nanoscopic systems ranging from single molecules to nano-electro-mechanical and nanofluidic systems. Researchers continue to look for new applications of nanotechnology. The concept of realizing independently operating, man-made and engineered devices measured in terms of nanometers has become reality and will continue to progress. And, as the field of biotechnology advances, the need to observe, measure, manipulate, control, and test substances and elements at the molecular level is ever more present.

One of the behavioral phenomena that exist in the world of nanotechnology is motion. Many aspects of the nanoworld are continuously in motion. The nature of the motion is directly related to the physical characteristics and environment to which the nanoscale elements and structures are subjected. The ability to detect, observe, measure, and control such motion at the nanoscale is important to the continuation of research and development of new products and design methods. Modern instrumentation and research techniques have difficulty with the accurate and reliable detection of motion, particularly rotational motion, in the nanometer range.

Attempts have been made to detect and measure rotational motion of small particles by observing changes in the orientation of the particle over time under a microscope. For example, the F1-ATPase enzyme has been observed to exhibit rotational motion along its axis by using fluorescence microscopy to visualize time-dependent changes in the orientation of fluorescently labeled actin filaments, a protein which is about 0.5 to 4 μm long, attached to the rotating shaft of the enzyme. Other research has measured the rotation of anisotropically patterned fluorescent polymer microspheres in the range of 2 to 4 μm in diameter. The particles of interest possess sufficient anisotropy to allow its orientation to be seen under the microscope.

Alternatively, if a particle rotates about an axis that is not an axis of symmetry of the particle, then its rotation can be measured by tracking the centroid of the particle's image. The rotation of a 1 μm polystyrene sphere attached to the shaft of the F1-ATPase molecule has been measured by detecting the displacement of the centroid of the sphere's image due to the slight eccentricity in the shaft's rotation.

At the nanoscale, the direct approach to detecting rotational motion using a light-based microscope is usually ineffective, since the diffraction limit of the light makes it difficult to resolve features, and hence determine the orientation, of nanoscopic objects. That is, the magnitude of the change in position of the object is less than the diffraction limit of the light used to measure it.

The single-molecule fluorescence polarization spectroscopy and the centroid-tracking method have limitations in that the signal emitted by a single fluorophore is weak. Fluorescence polarization spectroscopy requires a sensitive optical detection system. In addition, the probe is susceptible to photo-bleaching. Finally, the intensity of emission of a single fluorophore fluctuates. Single-molecule fluorescence polarization spectroscopy cannot distinguish such fluctuations from those due to the rotation of the fluorophore, making the method susceptible to noise. The centroid-tracking method works only for off-axis rotation involves time-consuming, off-line image analysis. In general, it is difficult to observe rotation of a circular object at any scale when viewed along the axis of rotation unless the rotation of the object is eccentric to the axis of rotation and/or the rotating object has an asymmetric shape.

SUMMARY OF THE INVENTION

In one embodiment, the present invention is a method of detecting motion in nanoscale structures comprising the steps of providing a molecular structure having a rotating arm, attaching a nanoparticle to the rotating arm of the molecular structure so that the nanoparticle rotates with the rotating arm of the molecular structure, exposing a light to the nanoparticle, wherein a first surface of the nanoparticle scatters a first wavelength of the light when the nanoparticle is in a first position and a second surface of the nanoparticle scatters a second wavelength of the light when the nanoparticle is in a second position, and filtering the first and second wavelengths of the light through a polarizing filter to detect rotational motion by observing alternating first and second wavelengths of the light.

In another embodiment, the present invention is a method of detecting a substance comprising the steps of attaching a detection DNA stand between a nanoparticle and a rotating portion of a molecular structure, hybridizing a target DNA strand corresponding to the substance to be detected to the detection DNA strand if the target DNA strand matches the detection DNA strand to form a structural link between the nanoparticle and the molecular structure, exposing a light to a first surface of the nanoparticle to scatter a first wavelength of the light, exposing a light to a second surface of the nanoparticle to scatter a second wavelength of the light, filtering the first and second wavelengths of the light, and detecting presence of the substance upon observing alternating first and second wavelengths of the filtered light.

In yet another embodiment, the present invention is a nanoscale motion detector comprising a molecular structure having a rotating portion. A nanoparticle is coupled to the rotating portion of the molecular structure. A light source is incident to a first surface of the nanoparticle to scatter a first wavelength of the light when the nanoparticle is in a first position and further incident to a second surface of the nanoparticle to scatter a second wavelength of the light when the nanoparticle is in a second position. A polarizing filter filters the first and second wavelengths of the light. The rotation motion is detected by observing first and second wavelengths of the filtered light.

BRIEF DESCRIPTION OF THE DRAWINGS

FIG. 2a illustrates the gold nanorod is shown in position A;
FIG. 2b illustrates the gold nanorod is shown in position B;
FIG. 2c illustrates the gold nanorod is shown in position C;
FIG. 2d illustrates the gold nanorod is shown in position D.

DETAILED DESCRIPTION OF THE DRAWINGS

The present invention relates to the detection and measurement of rotational motion at the nanometer level, that is, in the scale between 1 and 1000 nanometers, using anisotropic metal nanoparticle probes. The applications involved in characterizing and monitoring nanoscopic systems vary from single molecules to nano-electro-mechanical, nanofluidic systems, and other nanotechnologies. The present invention can be used to observe the physical and behavioral characteristics of a single molecule. Another application provides for detection of the presence of specific substances.

Figure 1:
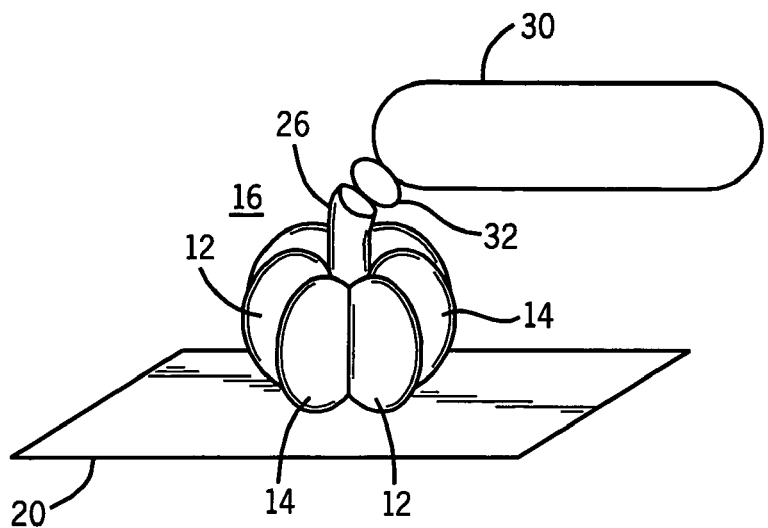
FIG. 1 illustrates a representation of the F1-ATPase enzyme.

Many enzymes are known to behave as molecular motors, i.e., molecular structures that produce rotation motion. The molecular motors can be biological in origin or chemically synthesized. One such molecular motor is the F1-ATPase enzyme as represented in FIG. 1. F1-ATPase enzyme 10 includes alpha-subunits 12 and beta-subunits 14 in its base structure 16. Base structure 16 is non-rotating and anchored or attached preferentially to surface 20. Surface 20 can be part of a DNA microarray, glass slide, or other dielectric substrate. Gamma-subunit 26 is molecularly coupled to base structure 16 and oriented upward, normal to surface 20. F1-ATPase enzyme 10 operates as a molecular motor with the alpha-subunits 12 and beta-subunits 14 inducing rotation in gamma-subunit arm 26. Thus, gamma-subunit arm 26 behaves as a drive shaft, oriented upward, perpendicular to surface 20, and rotating in response to activity in alpha-subunits 12 and beta-subunits 14. The rotation of gamma-subunit arm 26 is difficult to directly see under a microscope.

A gold nanorod 30 is attached to gamma-subunit arm 26 with a protein or other bonding molecule 32, such as avidin. Gamma-subunit arm 26 can attach to any part of gold nanorod 30, e.g., at either end, in the middle, or any point in-between. The bonding molecule 32 links gold nanorod 30 to gamma-subunit arm 26 so that the rotational motion of gamma-subunit arm 26 is imparted to gold nanorod 30. Gold nanorod 30 spins around with the rotational motion of gamma-subunit arm 26.

Metal nanoparticles, such as gold nanorod 30, are efficient absorbers and scatterers of light owing to collective oscillations of their conduction electrons known as surface plasmons. The number, position, and shape of the surface plasmon bands are determined by the kind of metal, the size and shape of the particle, and the dielectric constant of the surrounding medium. Non-spherical nanoparticles possess multiple surface plasmon modes. For example, rod-shaped nanoparticles exhibit two resonant modes, corresponding to their long and short axes, respectively.

Gold nanorod 30 is shaped as a rod, shaft, or cylinder with rounded or flat ends. Gold nanorod 30 is about 15-30 nm in diameter and about 60-80 nm in length along is symmetrical axis. In other embodiments, gold nanorod 30 has a length-diameter aspect ratio between 2.5:1 and 20:1. The rod-shaped nanoparticle is typically grown from a base wafer or sphere. Gold nanorod 30 exhibits optical anisotropy in that it has two surface plasmon resonances that correspond to the diameter and length of the shaft. The short axis corresponds to the transverse plasmon resonance of the rod. The long axis corresponds to the longitudinal plasmon resonance of the rod. The short and long axes of gold nanorod 30 scatter incident white light at different wavelengths as a function of the respective dimensions. The longer axis has greater surface area than the shorter axis. The short axis or end surface of gold nanorod 30 scatters light at a shorter wavelength due to the lesser surface area and the long axis or side surface of gold nanorod 30 scatters light at a longer wavelength due to its larger surface area. In one embodiment, the short axis of gold nanorod 30 scatters green light having a wavelength of about 520-570 nm, while the long axis scatters red light having a wavelength of 685-730 nm. Other relative dimensions of gold nanorod 30 will scatter incident white light at two different wavelengths.

Figure 2A:
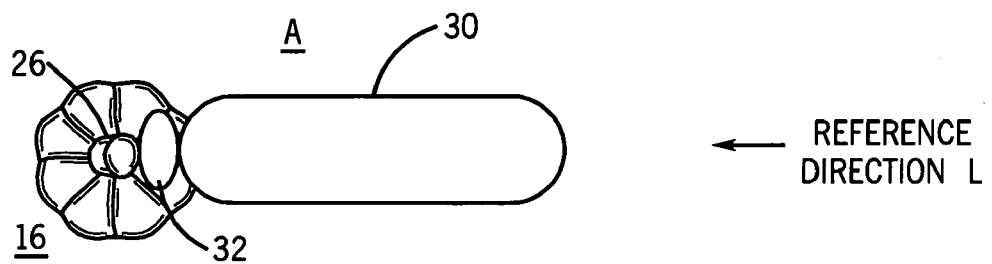
FIGS. 2a-2d illustrate the various positions of the gold nanorod during one revolution of the gamma-subunit arm.
Figure 2B:
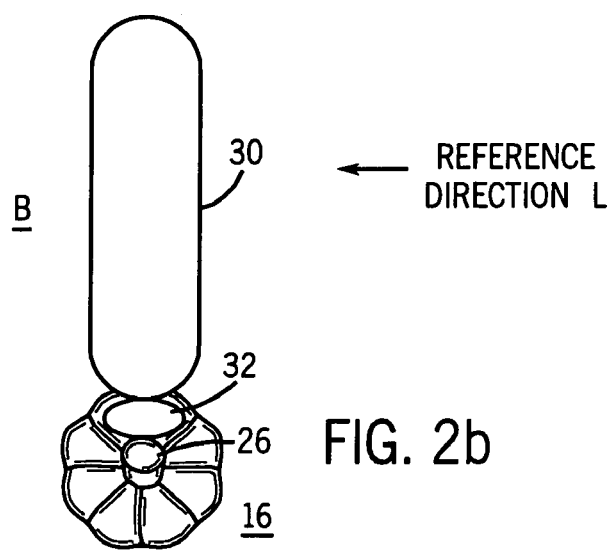
Figure 2C:
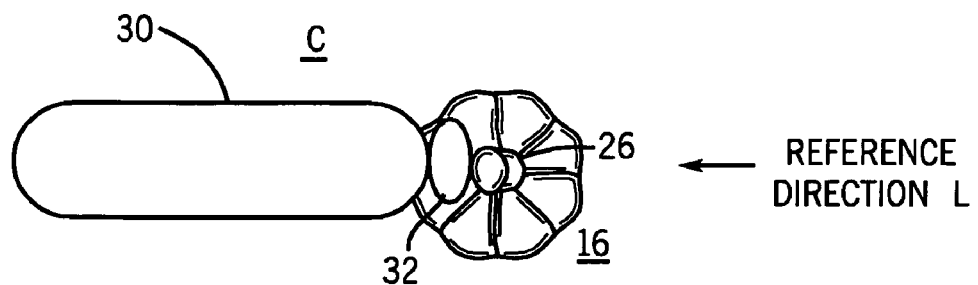
Figure 2D:
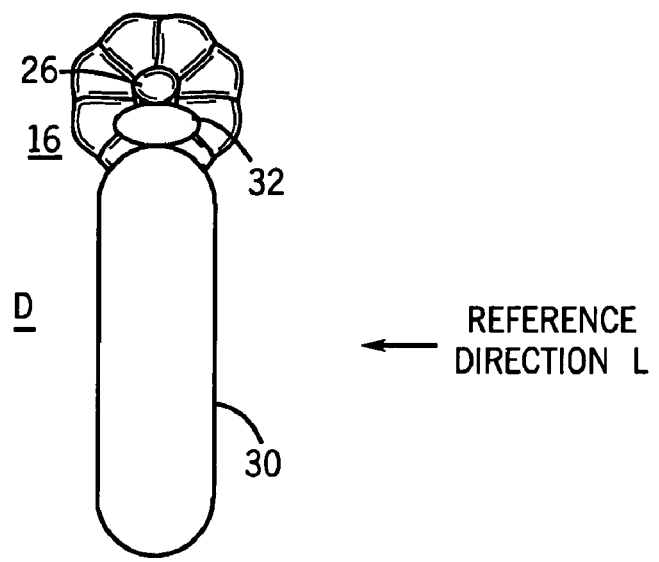

FIGS. 2a-2d illustrates a top view of gold nanorod 30 attached to F1-ATPase enzyme 10 at various positions A-D in one revolution of gamma-subunit arm 26. Drawing elements having a similar function are assigned the same reference numbers used in FIG. 1. In FIG. 2a, gold nanorod 30 is shown in position A with a first short axis or end surface oriented toward reference direction L. In FIG. 2b, a first long axis or side surface of gold nanorod 30 is shown in position B, oriented toward reference direction L. As the revolution of gamma-subunit 26 continues, a second short axis or end surface of gold nanorod 30 is shown in position C, oriented toward direction L, see FIG. 2c. In FIG. 2d, a second long axis or side surface of gold nanorod 30 is shown in position D, oriented toward reference direction L.

The above-described optical scattering characteristics of gold nanorod 30, in combination with its rotational motion imparted by gamma-subunit arm 26, provides for observation and measurement of physical characteristics and behavioral phenomena of molecular structures on the nanoscale. In a simplified view, a full spectrum, white-light source is generally directed in reference direction L. The white light photons strike gold nanorod 30 as a wave function and, depending on the orientation of gold nanorod 30 with respect to the incident angle of the photons, some wavelengths of the light will be scattered. With the given dimensions of gold nanorod 30, when the nanorod is in position A, a green light is scattered. When nanorod 30 is in position B, a red light is scattered. When nanorod 30 is in position C, a green light is scattered. When nanorod 30 is in position D, a red light is scattered.

The scattered light from gold nanorod 30 is polarized. The intensities of the red and green resonances depend on the relative orientation of the nanorod to the plane of polarization of the incident light. The rotating nature of gold nanorod 30, due to its connection to the spinning F1-ATPase molecular motor, results in an observable light that flashes or blinks alternating green and red. The intensity and rate of blinking of the red and green light is a function of the speed of rotation of gamma-subunit arm 26. By observing the red and green blinking light from gold nanorod 30, the rotational motion of F1-ATPase enzyme 10 can be detected and measured. The visible blinking light is much easier to observe than the physical rotating structure itself. Moreover, the polarized nature of the scattered wavelength causes gold nanorod 30 to go dark in between positions A-D. The flashing green and red lights are detectable, observable, and measurable using dark field microscopy.

Figure 3:
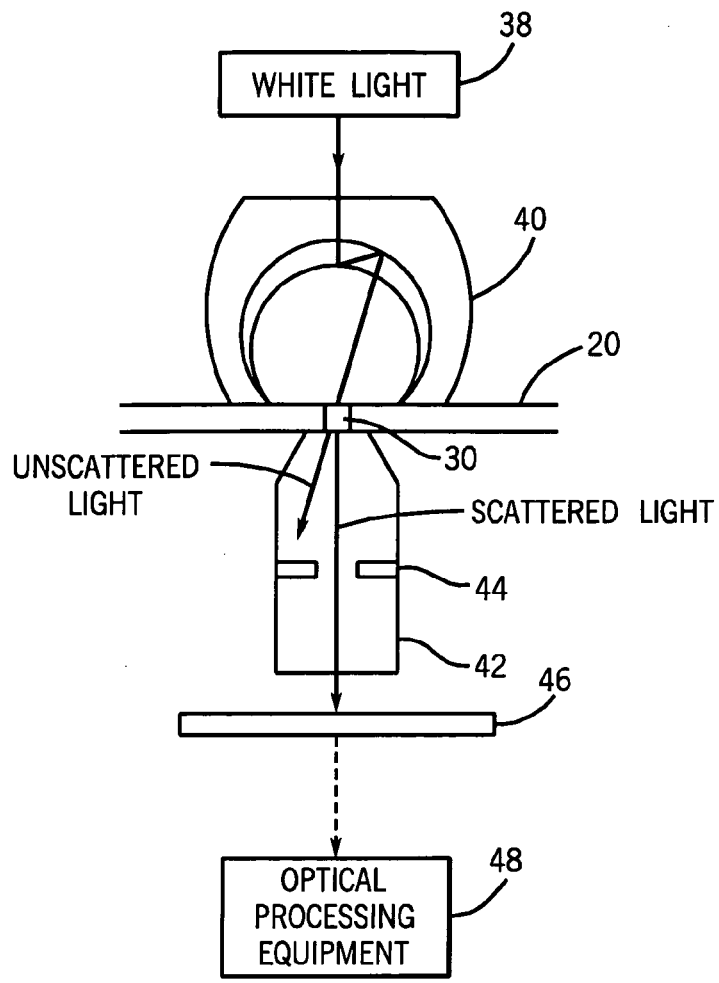
FIG. 3 is a dark field microscopy instrumentation setup used to detect the scattered light.

A dark field microscopy instrumentation setup for detecting, observing, and measuring the scattered light from gold nanorod 30 is shown in FIG. 3. A full spectrum white light from light source 38 is incident to dark field condenser and lens 40, which in turn alters the path of the light to create an oblique angle with respect to the long and short axes orientation of gold nanorod 30. The F1-ATPase enzyme 10 with attached gold nanorod 30 is positioned on slide surface 20. The F1-ATPase enzyme 10 and rotating gold nanorod 30 are exposed to the white light. The rotational motion of the F1-ATPase enzyme 10, and the corresponding rotation of gold nanorod 30, cause the red and green wavelengths of the incident light to scatter depending on the orientation of the nanorod. Red light scatters when the long axis is exposed to the white light and green light scatters when the short axis is exposed to the white light. The unscattered light continues on into objective lens 42 where it is blocked by iris 44. The wavelengths of the light, which are scattered by gold nanorod 30 pass through iris or aperture 44.

A polarizing filter 46 is positioned at the output of objective lens 42 and passes the wavelength of the scattered light which is aligned with the polarizing filter, and further blocks any light, scattered or not, which is not aligned with the polarizing filter. The scattered red light, which is aligned with polarizing filter 46, passes through the filter. Likewise, the scattered green light, which is aligned with polarizing filter 46, passes through the filter. The intensity of the red and green scattered light varies relative to the angle of polarization and has a maximum when the appropriate axis of gold nanorod 30 is parallel to the plane of polarization. When the light scattered from the long axis of gold nanorod 30 is aligned with polarizing filter 46 then red light is passed. When the light scattered from the short axis of gold nanorod 30 is aligned with polarizing filter 46 then green light is passed. No other light passes through polarizing filter 46, i.e., the output of polarizing filter 46 is otherwise dark.

The red and green lights are collected by optical processing equipment 48, which separates the red and green light into individual channels. MetaVue software is used to isolate, detect, observe, and measure the intensity of the red and green light. The F1-ATPase enzyme-induced rotation is observed as red and green blinking light through polarizing filter 46, due to surface plasmon resonance of gold nanorod 30. The alternating blinking red and green light has provided an observable and quantifiable representation of the physical and behavioral characteristics of the F1-ATPase enzyme 10, e.g., the blinking rate of the red and green light is a function of the speed of rotation of the F1-ATPase enzyme 10.

The gold nanorods can be used in a wide range of applications in nanoscience and nanotechnology where measurements of rotation are required. For example, the gold nanorod can be used to characterize and monitor the operation of biological nanomachines such as the F1-ATPase rotary biomolecular motor or man-made organic or nano-electro-mechanical devices. In addition, the gold nanorod is also suitable for measuring orientation, for example to sense whether a nanofluidic valve is in its open or closed position. Other potential applications are in the area of microfluidics and nanofluidics, where the metal nanoparticles can be used as probes to measure the local velocity, vorticity, and shear rate of the flow field.

In using anisotropic metal nanoparticles, such as gold nanorods 30, to detect rotation, a variation in the intensity of the longitudinal plasmon resonance results when the excitation polarization is fixed and the particle is free to rotate. The intensity of the longitudinal resonance encodes the orientation of the nanoparticle. For example, a gold nanorod rotating in a homogeneous medium will appear alternately red and green when viewed under dark field linearly polarized white light illumination as a result of successive excitation of the longitudinal and transverse surface plasmon resonances, respectively. A nanorod rotating near a surface will also appear to blink red-green, since the transverse surface plasmon, being smaller in amplitude, will only be visible to the eye when the intensity of the longitudinal plasmon is low. Since the metal nanoparticles scatter light strongly, the variations in scattering intensity can be picked up with a conventional, non-intensified charge-coupled device (CCD) camera. Moreover, since the intensity of the transverse plasmon resonance is nearly constant, it serves as an internal reference against which changes in the longitudinal plasmon resonance can be measured.

Rotation is detected by measuring variations in the intensity of a diffraction-limited spot of light. The detection method is applicable to both on and off-axis rotation. The nanoparticle probe is not susceptible to photo-bleaching, nor does it exhibit the fluctuations characteristic of single fluorophore probes. Also, with proper illumination, nanoparticles probes can be made to be much brighter than single fluorophores, which significantly reduces the demands on the sensitivity of the detection equipment or, alternatively, allows for the detection of much higher speed rotation. When the nanorod is rotating near a surface, the internal reference provided by the transverse plasmon resonance makes the method much more robust against sources of noise that cause variations in intensity of the longitudinal plasmon resonance unrelated to changes in orientation of the rod.

The nanoparticles can be ellipsoidal, rod-shaped, or other anisotropic shapes. The nanoparticles can be made of pure metals or alloys, and can be coated with a different type of metal or other material like glass. The nanoparticles can be flat structures patterned onto a metalized surface, for example by means of e-beam lithography.

Figure 4:
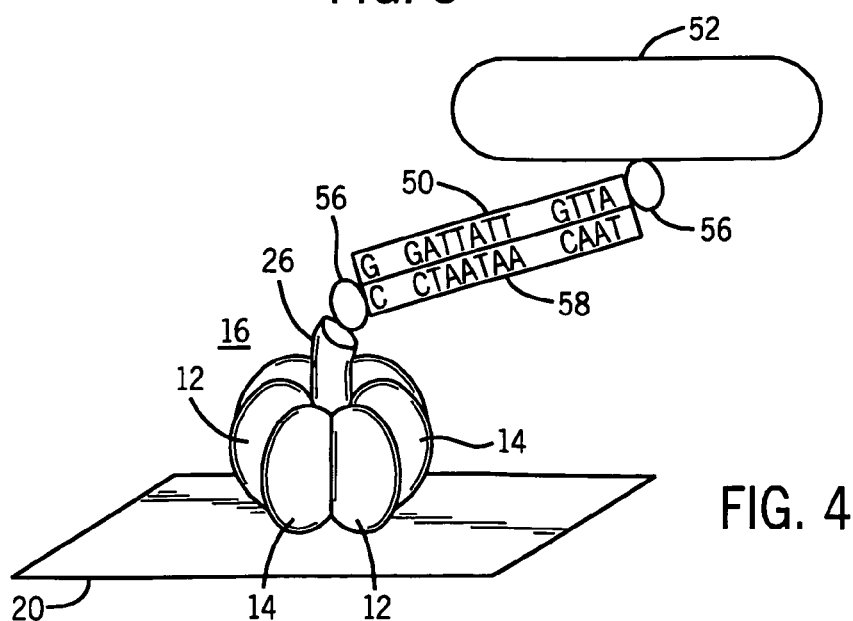
FIG. 4 is another embodiment for detecting a target substance using rotation of the gold nanorods (SEQ ID NOS: 1 and 2).

In another embodiment, the gold nanorods are used as part of a molecular semaphore to detect the presence of a single molecule of a substance. Instead of attaching the gold nanorod directly to the gamma-subunit arm, a known deoxyribonucleic acid (DNA) oligonucleotide or an antibody is attached between gold nanorod 52 and the rotating gamma-subunit arm 26 of the F1-ATPase enzyme 10, as shown in FIG. 4. The known DNA structure is the detectiong DNA strand 50 (SEQ ID NO: 1). A protein or bonding molecule 56, such as avidin, is used to anchor a first end of the detection DNA strand 50 (SEQ ID NO:2) to gamma-subunit arm 26 and further to anchor a second end of the detection DNA strand 50 (SEQ ID NO:1) to gold nanorod 52.

A sample of the target substance or molecule to be detected is introduced. The sequence of nucleotide base pairs is unique and defines the matching strand. If the DNA sequence of the target molecule matches DNA strand 50 (SEQ ID NO:1), i.e., the nucleotide bases of the target DNA strand correspond to the nucleotide bases of the detection DNA strand 50 (SEQ ID NO:1), such as shown in FIG. 4 (SEQ ID NO:2), then the target DNA strand will hybridize to the detection DNA strand 50 (SEQ ID NO:1) to form a bridge or linkage (See SEQ ID NO:2). If the nucleotide bases of the target DNA strand do not correspond to the nucleotide bases of the detection DNA strand 50, then the DNA of the target molecule will not hybridize to the detection DNA strand 50 and no bridge or linkage is formed. The hybridized DNA structure is the bridge, which provides a structural link between gamma-subunit arm 26 and gold nanorod 52 to cause gold nanorod 52 to rotate with the F1-ATPase enzyme 10. Without the formation of the linkage, the gold nanorod 52 will not rotate with the F1-ATPase enzyme. Therefore, if the DNA strands match, i.e., if the target substance is detected, then the bridge is formed and gold nanorod 52 rotates with gamma-subunit arm 26. If the DNA strands do not match, i.e., the target substance is not detected, then the linkage is not formed and gold nanorod 52 does not rotate with gamma-subunit arm 26. If the target substance is detected, then the gold nanorod will rotate with the F1-ATPase enzyme and the nanoscale motion detector will flash alternating red and green lights as discussed above. If the target substance is not detected, then the gold nanorod will not rotate with the F1-ATPase enzyme and the detector will remain dark. The observation of the red and green lights is the detection mechanism for the target substance.

The present substance detection technique provides for detection using a single molecule of the target substance and can be used to detect specific proteins, diseases, and biological warfare agents like Anthrax. Other applications include metabolites, proteomics, and a variety of drug testing.

A person skilled in the art will recognize that changes can be made in form and detail, and equivalents may be substituted for elements of the invention without departing from the scope and spirit of the invention. The present description is therefore considered in all respects to be illustrative and not restrictive, the scope of the invention being determined by the following claims and their equivalents as supported by the above disclosure and drawings.

What is claimed is:

1. A method of detecting motion in nanoscale structures, comprising:
    providing a molecular motor having a rotating arm;
    attaching a rod-shaped nanoparticle to the rotating arm of the molecular motor so that the nanoparticle rotates with the rotating arm of the molecular motor, wherein the nanoparticle is attached to the rotating arm of the molecular motor by a bridge formed in the presence of a DNA detection strand when hybridized to a target DNA strand, wherein the nanoparticle has a first surface and a second surface, and wherein the first surface has greater area than the second surface;
    exposing a light to the rod-shaped nanoparticle, wherein the nanoparticle scatters a first polarized wavelength of the light when the nanoparticle is in a first position and the nanoparticle scatters a second polarized wavelength of the light when the nanoparticle is in a second position;
    filtering the first and second polarized wavelengths of the light through a polarizing filter to detect rotational motion by observing alternating first and second wavelengths of the light.

2. The method of claim 1 wherein the rod-shaped nanoparticle is a gold nanorod.

3. The method of claim 2 wherein the first polarized wavelength of the light is longer than the second polarized wavelength of the light.

4. The method of claim 3 wherein the first polarized wavelength of the light is red light and the second polarized wavelength of the light is green light.

5. The method of claim 1 wherein the molecular motor is an F1-ATPase enzyme.

6. A method of detecting motion in nanoscale structures comprising:
- providing a molecular motor having a rotatable arm;
- attaching a nanoparticle having a first axis and a second axis to the rotatable arm of the molecular motor so that the nanoparticle rotates with the rotatable arm of the molecular motor, wherein the nanoparticle is attached to the rotatable arm of the molecular motor by a bridge formed in the presence of a DNA detection strand when hybridized to a target DNA strand, and wherein the first axis of the nanoparticle has a greater length than the second axis;
- providing light from a fixed location;
- altering a path of the light from the fixed location to create an oblique angle with respect to the first axis and second axis of the nanoparticle;
- exposing the light from the altered path onto the nanoparticle, the first axis of the nanoparticle scattering a first polarized wavelength of the light when the nanoparticle is in a first position of rotational motion, the second axis of the nanoparticle scattering a second polarized wavelength of the light when the nanoparticle is in a second position of rotational motion;
- providing an iris which passes the first and second polarized wavelengths of scattered light and blocks unscattered light;
- providing a polarizing filter which is aligned only to the first and second polarized wavelengths of the light wherein the polarizing filter blocks light not aligned with the filter;
- processing the first and second polarized wavelengths of light onto first and second channels, respectively; and
- detecting alternating first and second polarized wavelengths indicating motion of the nanoparticle and the molecular structure.

* * * * *

UNITED STATES PATENT AND TRADEMARK OFFICE
CERTIFICATE OF CORRECTION

| | | |
|---|---|---|
| PATENT NO. | : 8,003,316 B2 | Page 1 of 1 |
| APPLICATION NO. | : 10/538534 | |
| DATED | : August 23, 2011 | |
| INVENTOR(S) | : Wayne D. Frasch et al. | |

It is certified that error appears in the above-identified patent and that said Letters Patent is hereby corrected as shown below:

Please insert the following paragraph at Col. 1, line 19 before the heading "Background of the Invention":

--STATEMENT REGARDING FEDERALLY SPONSORED RESEARCH OR DEVELOPMENT

This invention was made with government support under GM050202 awarded by The National Institutes of Health. The government has certain rights in the invention.--

Signed and Sealed this
Nineteenth Day of June, 2012

David J. Kappos
*Director of the United States Patent and Trademark Office*

SEQUENCE LISTING

```
<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: target DNA

<400> SEQUENCE: 1
ggattattgt ta                                                    12

<210> SEQ ID NO 2
<211> LENGTH: 12
<212> TYPE: DNA
<213> ORGANISM: Artificial Sequence
<220> FEATURE:
<223> OTHER INFORMATION: detection DNA

<400> SEQUENCE: 2
cctaataaca at                                                    12
```